United States Patent [19]

Howard et al.

[11] Patent Number: 4,792,452
[45] Date of Patent: Dec. 20, 1988

[54] CONTROLLED RELEASE FORMULATION

[75] Inventors: John R. Howard; Peter Timmins, both of Merseyside, United Kingdom

[73] Assignee: E. R. Squibb & Sons, Inc., Princeton, N.J.

[21] Appl. No.: 78,505

[22] Filed: Jul. 28, 1987

[51] Int. Cl.$^4$ .............................................. A61K 9/30
[52] U.S. Cl. .................... 424/475; 424/468; 424/479; 424/480; 424/482; 514/54
[58] Field of Search ............... 424/468, 475, 479, 480, 424/482; 536/3; 514/54

[56] References Cited

U.S. PATENT DOCUMENTS 4,610,870 9/1986 Jain et al. ............................ 424/473

OTHER PUBLICATIONS

Data Sheet D1571, Alginate Industries Limited, London, "Gel Formation with Alginates".
"In vitro Evaluation of Alginate Gel Systems as Sustained Release Drug Delivery Systems", Stockwell, A. F. et al., Journal of Controlled Release 3 (1986) 167–175.

Primary Examiner—William R. Dixon, Jr.
Assistant Examiner—Anthony J. Green
Attorney, Agent, or Firm—Lawrence S. Levinson; Burton Rodney

[57] ABSTRACT

A controlled release pharmaceutical formulation is provided which releases a pharmaceutical of a basic character at a controlled rate regardless of the pH of the environment, which formulation includes a basic pharmaceutical, up to about 45% by weight of a pH dependent polymer which is a salt of alginic acid, such as sodium alginate, up to about 35% by weight of a pH-independent hydrocarbon gelling agent having a viscosity of up to about 100,000 centipoises in 2% solution at 20° C., binder and excipients.

20 Claims, No Drawings

CONTROLLED RELEASE FORMULATION

FIELD OF THE INVENTION

The present invention relates to a controlled release formulation for releasing a pharmaceutical of a basic character at a controlled rate regardless of the pH of the environment and which formulation includes up to about 45% by weight of a pH dependent polymer which is a salt of alginic acid, and a pH independent hydrocarbon gelling agent, such as hydroxypropylmethyl cellulose.

BACKGROUND OF THE INVENTION

The use of hydroxypropylmethyl cellulose as a rate controlling hydrophilic polymer in controlled release formulations is well-documented.

A major problem associated with most existing controlled release systems containing hydroxypropylmethyl cellulose and other pH independent rate controlling polymers is that they provide no control over drug release into media of differing pH, where drug solubility is dependent upon pH.

A sustained or controlled release product providing pH-independent drug release is essential to avoid problems of bioavailability variation during therapy if fluctuations in gastrointestinal pH can occur. There is, of course, the natural pH gradient down the gut from the acidity of the stomach, through the weakly acidic duodenum to the neutral environment of the small intestine. Superimposed on this are possible fluctuations in pH arising from dietary changes. For example, feeding or fasting have effects on stomach acidity and this would affect a product with pH-dependent drug release if it were taken with or between meals. Other pH changes can be drug induced. For example, the treatment of duodenal or gastric ulcer with $H_2$-receptor antagonists like cimetidine or ranitidine may markedly raise basal gastric pH.

Consistent sustained release drug product performance against all these challenges would be highly desirable.

Alginate based systems have been proposed as oral sustained release matrix dose forms. Gel formation in these systems is governed by an interaction between calcium ions and alginic acid. "Gel Formation iith Alginate", Data Sheet D1571, Alginate Industries Limited, London, discloses that "gel formation is obtained by steady and uniform release of calcium, or other cations capable of forming an insoluble alginate, into the alginate solution". Other workers (Stockwell, A. F. et al., Journal Controlled Release, 3 (1986) 167–175) have employed the calcium gelled alginate system in combination with $CO_2$ generating excipients to yield a tablet that floats on the gastric contents. Such systems are not intended to pass down the GI tract and release drug in variable pH environments.

DESCRIPTION OF THE INVENTION

In accordance with the present invention, a controlled release pharmaceutical formulation is provided from which a pharmaceutical of a basic character is released, at a controlled rate relatively independent of the pH of the environment such that in vivo consistent release is achieved throughout the gastrointestinal tract. The controlled release pharmaceutical formulation of the invention will preferably be in the form of a tablet and includes a pharmaceutical of a basic character; a pH-dependent polymer which is a water soluble salt of alginic acid in an amount of up to about 45% by weight depending upon the nature of the pharmaceutical present, preferably from about 15 to about 45% by weight and more preferably from about 20 to about 35% by weight of the formulation; a pH-independent hydrocolloid gelling agent having a viscosity within the range of from about 50 to about 100,000 centipoises and preferably from about 100 to about 15,000 centipoises in 2% solution a 20° C., in an amount of up to about 35% by weight, preferably within the range of from about 5 to about 20% by weight and more preferably from about 8 to about 17% by weight of the formulation; binder and excipients and other conventional tablet ingredients. The above formulation may optionally be coated with one or more film formers, employing one or more plasticizers, and one or more solvents and other conventional coating ingredients. The formulation of the invention will not contain calcium ions so there will be no calcium ions available to interact with the alginate salt.

It is theorized that upon oral ingestion of the sustained release tablet of the invention, in an acid aqueous environment, such as the stomach the pH-independent hydrocolloid gelling agent hydrates to form a gel layer at the surface of the tablet. At this low pH environment alginic acid is formed from the alginate salt and this modifies the gel layer around the tablet. Erosion of the gel layer gradually exposes more dry matrix that hydrates to replenish the gel layer. Drug dissolves in the gel layer and diffuses out into the surrounding aqueous environment. Some interaction between the basic drug and the alginic acid polymer may also be involved.

As pH is increased, with passage of the tablet from the stomach down the gastrointestinal tract, the alginic acid salt in the tablet becomes more soluble and the alginic acid formed in the stomach will be reconverted to a more soluble salt, and it will structure the hydrocolloid gelling agent gel layer less. Drug can diffuse more readily through the gel layer now and the ensuing increase in release rate from the matrix compensates for the reducing driving force for dissolution at the elevated pH values, where solubility of a basic drug is lower.

The controlled release formulation of the invention does not contain calcium ions, or sodium bicarbonate or other carbon dioxide-producing material and thus will not float in the stomach.

The pharmaceutical of a basic character will be present in the formulation of the invention in an amount of up to about 75% by weight and preferably up to about 60% by weight.

A wide variety of medicaments (of basic nature) which are orally administered in tablet form can be used in the form of tablets prepared according to this invention. These include, for example, adrenergic agents such as salts of ephedrine, desoxyephedrine, phenylephrine, epinephrine, salbutamol, terbutaline and the like, cholinergic agents such as salts of physostigmine, neostigmine and the like, antispasmodic agents such as salts of atropine, methantheline, papaverine and the like, curariform agents such as salts of chlorisondamine and the like, tranquilizers and muscle relaxants such as salts of fluphenazine, thioridazine, trifluoperazine, chlorpromazine, triflupromazine and the like, antidepressants like salts of amitriptyline, nortriptyline, and the like, antihistamines such as salts of diphenhydramine, chlorpheniramine, dimenhydrinate, tripelennamine, perphenazine, chlorprophenazine, chlorprophenpyridamine and the like, cardioactive agents such as salts of verapamil, diltiazem, gallapomil, cinnarizine, propranolol, metoprolol, nadolol, and salts of any of the following: antimalarials such as chloroquine and the like, analgesics such as propoxyphene, meperidine and the like, etc. Other therapeutic agents having the same or different physiological activity can also be employed in pharmaceutical preparations within the scope of the present invention.

The invention is particularly adapted for controlled release tablets containing the calcium channel blocker verapamil (usually formulated in the form of its hydrochloride).

The amount of salt of alginic acid that will be present will depend upon the pharmaceutical present and could range up to less than about 50% by weight of the tablet core. Usually, the salt of alginic acid will be present in an amount within the range of from about 15 to about 45% by weight and preferably from about 20 to about 40% by weight of the formulation. Such salt will preferably take the form of an alkali metal salt such as sodium alginate or potassium alginate or ammonium alginate, and preferably sodium alginate. The salt of alginic acid will have a viscosity of up to about 500 or more centipoises in 1% solution at 25° C. and preferably from about 4 to about 350 centipoises. It will be appreciated that mixtures of the same or different alginic acid salts of the same or different viscosities may be employed herein.

The alginic acid salt will be employed in a weight ratio to the hydrocolloid gelling agent of within the range of from about 0.1:1 to about 10:1 and preferably from about 0.4:1 to about 8:1.

The hydrocolloid gelling agent, may be of the compressible or non-compressible type, and is essential to the practice of the invention in that it absorbs water, swells and forms a gel. It will be of the type to provide a viscosity of 50 to 100,000 centipoises in a 2% aqueous solution at 20° C., will have a molecular weight ranging from about 80,000 to about 300,000. Thus, the hydrocolloid is provided in an amount of up to about 35% by weight of the formulation and preferably from about 3 to about 15%.

The hydrocolloid for use in the core will have a viscosity of more than 50 centipoises as indicated above, and will preferably comprise cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million). Preferred are sodium carboxymethyl cellulose, methyl cellulose, hydroxypropylmethyl cellulose and carboxypolymethylene. However, it is to be understood that any hydrocolloid may be employed in the present invention, such as, for example, gum acacia, guar gum, gum tragacanth, gum xanthan, an alkali metal carageenate, or mixtures thereof.

Other examples of suitable hydrocolloids are set out in U.S. Pat. No. 4,140,755 to Sheth et al.

Where both the medicament and/or the hydrocolloid gelling agent are non-compressible, it is preferred that the formulation of the invention, such as a tablet, also includes one or more non-swellable binders which bind the core ingredients to prevent premature tablet disintegration and promote proper release rate. The binders will be present in the tablet in an amount within the range of from 0 to about 8% and preferably from about 0.5 to about 5% by weight of the tablet. Examples of such binders suitable for use herein include, but are not limited to, polyvinylpyrrolidone (molecular weight ranging from 5000 to 700,000 and most preferably about 40,000), lactose, gelatin, hydropropyl methyl cellulose having a viscosity of 3 to 15 centipoises, hydrolyzed animal protein, starches such as corn starch, modified corn starch, sugars, gum acacia, microcrystalline cellulose and the like.

The sustained release tablets will also include additional edible non-toxic ingredients as conventionally employed in solid medicinal dosage forms. Thus, the tablets of the invention may include one or more excipients in conventional amounts, such as lactose, sugar, microcrystalline cellulose, wood cellulose, mannitol, sorbitol, one or more tableting lubricants in an amount within the range of from about 0.25 to about 8% by weight of the tablet, and preferably from about 0.5 to about 4% by weight of the tablet, such as magnesium stearate, stearic acid, palmitic acid, talc, carnauba wax and the like. Other conventional ingredients which may optionally be present include preservatives, stabilizers, anti-adherents or silica flow conditioners or glidants, such as Syloid brand silicon dioxide as well as FD&C colors.

A coating layer may be applied over the tablet for usual pharmaceutical purposes.

The coating or film forming layer will also include one or more plasticizers, such as triethyl citrate, diethyl phthalate, polyethylene glycol (molecular weight 300 to 4000), propylene glycol, glycerin, butyl phthlate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1- trichloroethane.

Where a color is employed, the color will be applied together with the film former, plasticizer and solvent composition.

Finished tablets having a total weight of up to 1 gm or even more can be prepared. Of this total weight, the core will comprise from about 85 to about 98% by weight of the tablet, the coating layer will comprise from about 15 to about 2% by weight of the tablet, with the medicament comprising up to about 75% or more by weight of the tablet core.

Preferred controlled release tablet formulations of the invention will include the following:

| Ingredient | % by Weight |
| --- | --- |
| Medicament (basic) (e.g., verapamil) | 20 to 60 |
| Alginic acid basic salt (such as Na alginate - viscosities ranging from 5 to 350 at 20° C. in 1% solution) | 15 to 45 |
| Hydrocolloid gelling agent (such as hydroxypropylmethyl cellulose, e.g., Methocel E4M, viscosity of 4000 cps at 2% solution at 20° C.) | 3 to 15 |
| Binders (such as hydroxypropylmethyl cellulose, Methocel E5, | 0.5 to 5 |

| -continued | |
|---|---|
| Ingredient | % by Weight |
| viscosity of 5 cps at 2% solution at 20° C.) | |
| Excipients qs to 100% | |

The sustained release tablets of the invention may be prepared as follows. All of the powders except the lubricant and binder are dry mixed in a suitable blender. Water, with the binder in solution, is added to moisten the mass in a suitable blender and the mass granulated, for example by forcing through a screen of suitable mesh size. Thereafter, the tabletting lubricant and flow agent, if present, are added and the mixture is thoroughly mixed and then compressed into tablet cores. If desired, a coating solution formed of film formers, plasticizers and one or more solvents may then be sprayed on the cores to form the tablets of the invention.

The following Examples represent preferred embodiments of the present invention.

EXAMPLE 1

A sustained release formulation capable of slowly releasing the calcium channel blocker verapamil HCl regardless of the pH of the environment for a period of up to 10 to 12 hours or more and having the following composition was prepared as described below.

| Ingredient | Amount (kg) | Per Dosage Unit (mg) |
|---|---|---|
| Tablet Composition | | |
| Verapamil hydrochloride | 0.505 | 240 |
| Sodium alginate (300 cps) | 0.284 | 135 |
| Hydroxypropylmethyl cellulose (Methocel E4M viscosity of 4000 cps) (hydrophilic polymer) | 0.094 | 45 |
| Avicel pH 101 (microcrystalline cellulose) | 0.070 | 33.2 |
| Lactose | 0.0175 | 8.3 |
| Hydroxypropylmethyl cellulose (binder - Methocel E5) | 0.0159 | 9.0 |
| Magnesium stearate (lubricant) | 0.0095 | 4.5 |
| Purified water q.s. | | |

The q.s. ingredient was for processing purposes only and does not appear in the final product.

Verapamil hydrochloride, hydroxypropylmethyl cellulose, sodium alginate, microcrystalline cellulose and lactose were dry blended for 5 minutes in a suitable blender. The powders were then wet massed using binder in aqueous solution and the mix passed through a 10# screen. The granules were dried and the magnesium stearate added thereto.

The so-formed mixture was then thoroughly mixed and compressed into tablets each weighing 475 mg.

The so-formed sustained release tablet of the invention was found to undergo slow and uniform release of drug over a 15 hour period, regardless of the pH of the environment.

EXAMPLES 2 and 3

In a manner similar to that described in Example 1, 475 mg tablets each containing 240 mg verapamil hydrochloride and 633 mg tablets each containing 320 mg verapamil hydrochloride are prepared.

EXAMPLE 4

A propranolol tablet in accordance with the present invention is prepared following the procedure of Example 1 except substituting propranolol for the verapamil hydrochloride.

EXAMPLE 5

A trifluoperazine HCl tablet in accordance with the present invention is prepared following the procedure of Example 1 except substituting trifluoperazine HCl for the verapamil hydrochloride.

A diltiazem HCl tablet in accordance with the present invention is prepared following the procedure of Example 1 except substituting diltiazem HCl for the verapamil hydrochloride.

It will be understood that with respect to the formulations prepared in Examples 4, 5 and 6, the ratio of HPMC/alginate and viscosity grade of alginate may be modified to yield drug release more or less independent of environmental pH, consistent with the in vivo needs of the product.

EXAMPLE 7

A metoprolol tartrate salt tablet in accordance with the present invention is prepared following the procedure of Example 1 except substituting metoprolol tartrate for verapamil hydrochloride.

EXAMPLE 8

A verapamil tablet containing sodium alginates of different viscosities having the following composition was prepared as described in Example 1.

| Ingredient | Amount/Tablet mg |
|---|---|
| Verapamil HCl | 240 |
| Sodium alginate 9 cps (measured at 20° C. in 1% solution) | 90 |
| Sodium alginate 300 cps (measured at 20° C. in 1% solution) | 45 |
| Hydroxypropylmethylcellulose 4000 cps (E4M) | 45 |
| Hydroxypropylmethyl cellulose 5 cps (E5) | 9 |
| Microcrystalline cellulose | 33.2 |
| Lactose BP | 8.3 |
| Magnesium stearate | 4.5 |
| | 450.0 mg |

What is claimed is:

1. A controlled release pharmaceutical formulation from which a pharmaceutical of a basic character is released at a controlled rate irrespective of the pH of the environment, consisting essentially of a pharmaceutical of a basic character, a pH-dependent polymer which is a salt of alginic acid, in an amount of from about 15 to about 45% by weight of the formulation, said salt of alginic acid having a viscosity of within the range of from about 4 to about 500 centipoises in 1% solution at 25° C.; a pH-independent hydrocolloid gelling agent having a viscosity within the range of from about 50 to about 100,000 centipoises in 2% solution at 20° C., in an amount within the range of from about 3 to about 35% by weight of the formulation, and binder, said formulation being free of calcium ion.

2. The formulation as defined in claim 1 wherein the pH-dependent salt of alginic acid is employed in a weight ratio to the pH-independent hydrocolloid gelling agent of within the range of from about 0.1:1 to about 10:1.

3. The formulation as define in claim 1 wherein said pH-dependent salt of alginic acid is employed in an amount within the range of from about 20 to about 35% by weight of the formulation and the pH-independent hydrocolloid gelling agent is employed in an amount within the range of from about 3 to about 20% by weight of said formulation.

4. The formulation as defined in claim 1 wherein said pharmaceutical of a basic character is employed in an amount of from about 20 to about 75% by weight of said formulation.

5. The formulation as defined in claim 1 in the form of a tablet.

6. The formulation as defined in claim 1 wherein said pharmaceutical of a basic character is a calcium antagonist.

7. The formulation as defined in claim 6 wherein said calcium antagonist is a salt of verapamil, a salt of diltiazem, a salt of nicardipine, a salt of nifedipine, a salt of gallapomil or a salt of cinnarizine.

8. The formulation as defined in claim 1 wherein said pharmaceutical of a basic character is a beta blocker, antihistamine, sympathomimetic, beta adrenergic agonist or bronchodilator, or central nervous system drug.

9. The formulation as defined in claim 8 wherein said beta blocker is a salt of propranolol, a salt of metoprolol, or a salt of nadolol, said antihistamine is a salt of chlorpheniramine, a salt of diphenhydramine, said sympathomimetic is a salt of phenylpropanolamine or a salt of pseudoephedrine, said beta adrenergic agonist is a salt of salbutamol, or a salt of terbutaline, and said central nervous system drug is a salt of thioridazine, a salt of trifluoperazine, or chlorpromazine.

10. The formulation as defined in claim 1 wherein said hydrocolloid gelling agent is hydroxypropylmethyl cellulose, methyl cellulose, hydroxypropyl cellulose, or a mixture of two or more of such hydrocolloid gelling agents.

11. The formulation as defined in claim 1 wherein said binder is hydroxypropylmethyl cellulose having a viscosity of from about 5 to about 15 centipoises, hydrolyzed gelatin or polyvinyl pyrrolidone.

12. The formulation as defined in claim 1 further including one or more excipients.

13. The formulation as defined in claim 12 wherein said excipient is microcrystalline cellulose, lactose, sugar, mannitol, sorbitol, inorganic salts or cellulose.

14. The formulation as defined in claim 1 further including a lubricant.

15. The formulation as defined in claim 14 wherein said lubricant is magnesium stearate or stearic acid.

16. The formulation as defined in claim 1 wherein said salt of alginic acid is sodium alginate or potassium alginate.

17. The formulation as defined in claim 1 wherein the salt of alginic acid has a viscosity of within the range of from about 4 to about 350 centipoises in 1% solution at 25° C.

18. The formulation as defined in claim 1 containing alginic acid salts of two different viscosities.

19. The formulation as defined in claim 1 further including a coating layer.

20. The formulation as defined in claim 1 wherein said pharmaceutical of a basic character is verapamil hydrochloride, said salt of alginic acid is sodium alginate, said hydrocolloid gelling agent is hydroxypropylmethyl cellulose having a viscosity of from about 50 to about 100,000 centipoises, said binder is hydroxypropylmethyl cellulose having a viscosity of from about 5 to about 15 centipoises, further including microcrystalline cellulose and lactose as binders-excipients and further including magnesium stearate as a lubricant.

* * * * *